United States Patent
Yamamoto et al.

(10) Patent No.: US 6,497,154 B1
(45) Date of Patent: Dec. 24, 2002

(54) METHOD OF PREPARING SLAG SAMPLE FOR X-RAY FLUORESCENCE ANALYSIS AND SAMPLER FOR USE IN THE SAME

(75) Inventors: Akira Yamamoto, Chiba (JP); Noriko Makiishi, Chiba (JP); Wataru Tanimoto, Chiba (JP)

(73) Assignee: Kawasaki Steel Corporation, Hyogo (JP)

( * ) Notice: Subject to any disclaimer, the term of this patent is extended or adjusted under 35 U.S.C. 154(b) by 0 days.

(21) Appl. No.: 09/582,646

(22) PCT Filed: Aug. 20, 1999

(86) PCT No.: PCT/JP99/04488

§ 371 (c)(1),
(2), (4) Date: Aug. 23, 2000

(87) PCT Pub. No.: WO00/26635

PCT Pub. Date: May 11, 2000

(30) Foreign Application Priority Data

Oct. 29, 1998 (JP) .............................. 10-307985

(51) Int. Cl.$^7$ ............................ G01N 1/12; G01N 1/28; G01N 23/00
(52) U.S. Cl. ........................ 73/863; 73/864; 73/DIG. 9; 378/44
(58) Field of Search ....................... 73/864.58, 864.59, 73/DIG. 9, 863, 864, 864.51; 378/44, 45, 46, 47, 48, 49, 50

(56) References Cited

U.S. PATENT DOCUMENTS

| | | | | |
|---|---|---|---|---|
| 4,590,809 A | * | 5/1986 | Otsubo et al. | ........... 73/863.53 |
| 5,131,633 A | * | 7/1992 | Brinker | ................ 73/DIG. 9 X |
| 5,156,799 A | * | 10/1992 | Baerts | ................. 73/864.56 X |
| 5,435,196 A | * | 7/1995 | Cassidy | ............... 73/DIG. 9 X |

FOREIGN PATENT DOCUMENTS

| | | | | |
|---|---|---|---|---|
| JP | 54-690 | * | 1/1979 | ............ G01N/1/10 |
| JP | 59-138956 A | * | 8/1984 | ................... 436/75 |
| JP | 60-131858 U | * | 9/1985 | ................... G01N/1/13 |
| JP | 9-222426 A | * | 8/1997 | ............ G01N/1/10 |
| JP | 10-170411 A | * | 6/1998 | ............ G01N/1/10 |
| JP | 10-267915 A | * | 10/1998 | ............ G01N/1/10 |
| WO | WO 99/28727 A1 | * | 6/1999 | ............ G01N/1/12 |

OTHER PUBLICATIONS

TDB–Acc–No.: NN6506178 "Slag Thickness and Weight Determination" IBM Technical Disclosure Bulletin, vol. 8, No. 1, p. 178, Jun. 1965.*

Derwent–Acc–No.: 1991–013273 Abstract & Clipped image of SU 1543290 A, Inventor Antonou et al "Liquid Slag Sampler—. . . ", Feb. 1990.*

* cited by examiner

Primary Examiner—Thomas P. Noland
(74) Attorney, Agent, or Firm—Young & Thompson

(57) ABSTRACT

A metallic hollow polygonal column having a smooth outer surface is immersed into a molten slag and immediately pulled up. The contact plane of the slag adhered on the outer surface of the hollow polygonal column is used as the analytical plane. The method of the hollow column has a thickness of 3 mm or greater.

18 Claims, 1 Drawing Sheet

METHOD OF PREPARING SLAG SAMPLE FOR X-RAY FLUORESCENCE ANALYSIS AND SAMPLER FOR USE IN THE SAME

TECHNICAL FIELD OF THE INVENTION

The present invention relates to a method for preparing an analytical sample of the slag which generate in the refining process of metals and to an apparatus for preparing the same. In particular, the present invention relates to a method for preparing a slag sample from slags that are generated in the refining process of steel, which is subjected to an on-line rapid analysis using fluorescent X-ray spectroscopy, and to a sampler for use in the same.

BACKGROUND OF THE INVENTION

In the case of refining a metal such as in the smelting process of steel, it is important to control the. composition of the slag so that a metal having the targeted composition can be obtained. Accordingly, it is preferred to properly control the refining process based on the results obtained by performing slag analysis during the smelting process. Furthermore, in a process of effectively reusing the ash resulting from a combustion furnace for disposing wastes, it is also desired .to control the slag composition.

For the slag analysis, generally used method is glass bead fluorescent X-ray analysis, because this method enables the analysis of a plurality of elements simultaneously and at a high precision. More specifically, this method comprises preparing a homogeneous glass-like sample by crushing the slag and fusing the size-reduced slag using a flux, for instance, sodium borate, at an amount about 10 times as large as that of the slag, and then subjecting the sample to fluorescent X-ray analysis. This method is characterized in that it is less influenced by the coexisting elements and that, a high analytical precision is achievable; however, this method suffers disadvantages as such that the sample preparation requires operations such as crushing, weighing, and fusing, and that the total analytical procedure generally requires a time duration of 30 minutes or longer.

In the light of such circumstances, the briquette method is sometimes employed as a simplified analytical method. As compared with the glass bead method, the time necessary for carrying out this method can be shortened because the operations of weighing and fusing can be eliminated; still, however, the method still consumes for at least 25 to 30 minutes because the vessel for use in crushing requires pre-washing using the crushed sample. Furthermore, even if the aforementioned glass bead method or the briquette method should be assembled as an automated system, it is still difficult to shorten the analytical time to 20 minutes or shorter, and hence, at present, the analytical results obtained on the slag cannot be immediately reflected to the refining operation.

As a means for overcoming the problems above, in JP-A-Hei9-166589 (the term "JP-A" as referred herein signifies "an unexamined published Japanese patent application") is disclosed a method comprising directly subjecting the sampled slag to fluorescent X-ray analysis. This method comprises inserting a sampler having a large flat surface into the molten slag layer to thereby allow the slag to adhere on the flat surface, pulling up the sampler from the slag layer, stripping off the solidified slag, and subjecting the plane of the slag which was not brought into contact with the sampler to the fluorescent X-ray analysis. However, in the method above, it is found that the contact plane of the slag with the sampler undergoes cooling at a different cooling rate as compared with that of the plane which was not brought into contact with the sampler. Thus, segregation in composition of the slag occurs within the non-contact plane, i.e., the plane that was cooled at a rate slower than that in the contact plane. Accordingly, in the aforementioned methods, the analytical plane, which was the last to be solidified, exhibits a greatly differed composition as compared with the average composition of the slag, and hence fails to give the accurate average slag composition. Furthermore, in a refining process of steel, for instance, it is not always possible to obtain a flat analytical plane, because the viscosity of the slag fluctuates depending on the type of the steel or on the operational stage. This also is an advantageous which leads to an inferior analytical precision.

On the other hand, in JP-A-Hei10-170411 is disclosed a technique comprising inserting a columnar sample 20 mm or longer in side and having at least one flat plane 10 mm or larger in diameter into a slag layer, rapidly pulling up the sampler, stripping off the solidified slag, and subjecting the plane there of in contact with the sampler to fluorescent X-ray analysis.

In a practical refining process, however, it is not possible to surely sample a vigorously fluctuating slag by using the sampler above having such small sides each about 20 mm in length. Accordingly, in a practical process, a sampler increased in size is used, for instance, a sampler at least 50 mm in length, 50 mm in width, and 500 mm in height, is employed. In this case, the sampler becomes as heavy as to weight 10 kg or more; that is, the sampling operation by hand is no longer a simple method. That is, the operatability and practical advantages in the operation site become greatly impaired.

In the light of the circumstances above, an object of the present invention is to overcome the problems of the conventional technology, and to provide a method of sample preparation for use in the smelting process of fused metal such as steel, which enables a rapid and accurate analysis of slag, and which is capable of providing on-line instructions during the refining operation based on the analyzed results. It is also an object of the present invention to provide a sampler which can be easily handled for use in the method.

DISCLOSURE OF THE INVENTION

According to the present invention, there is provided a method of preparing a slag sample for use in fluorescent X-ray analysis, which comprises immersing a metallic hollow polygonal column having smooth outer surface into a molten slag and immediately pulling it up, and then using the contact plane of the slag adhered on the outer surface of the hollow polygonal column as the analytical plane. In the method of preparing the slag sample for use in fluorescent X-ray analysis above, it is preferred to use a slag sampler for fluorescent X-ray analysis below as the hollow polygonal column.

More specifically, the present invention provides as the sampler for use in the fluorescent X-ray analysis, a hollow polygonal column comprising a smooth outer surface, provided that the member constituting the hollow polygonal column is a metal having a thickness of 3 mm or greater.

In the sampler for fluorescent X-ray analysis above, the outer surface of said hollow polygonal column is preferably coated with a releasing agent, and said hollow polygonal column is preferably a hollow tetragonal column.

PREFERRED EMBODIMENTS OF THE INVENTION

Figure 1:
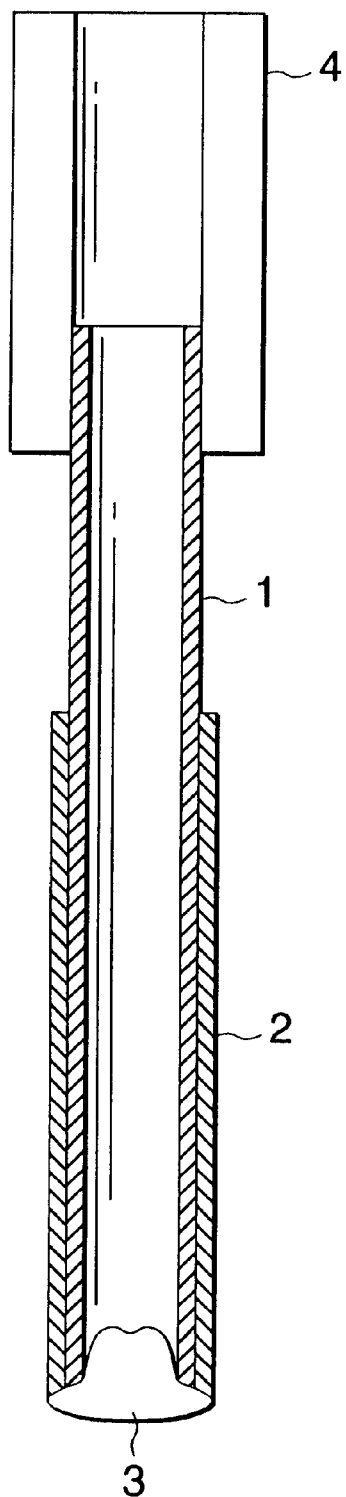
FIG. 1 is a longitudinal cross section showing an example of a slag sampling apparatus according to the present invention.

In the present invention, the sample preparation method comprises immersing a metallic hollow polygonal Column having smooth outer surface into a molten slag and immediately pulling it up, and then using the contact plane of the slag adhered on the outer surface of the hollow polygonal column as the analytical plane. That is, by immersing and immediately pulling up the metallic hollow polygonal column, the metallic hollow polygonal column above functions as a quenching body which rapidly cools the slag adhered thereon, thus solidifying and fixing the slag on the outer surface of the column. In performing fluorescent X-ray analysis, the slag sample must be quenched to obtain a sample solidified in a glassy state (an amorphous state) maintaining the composition on melting, however, by taking into consideration that the analytical depth in fluorescent X-ray analysis is merely several micrometers from the surface, the thickness to be quenched into a glass state can be confined to a range of several micrometers. In the present invention, accordingly, a lightweight hollow polygonal column made of a relatively thin metal plate is used in the place of a heavy solid cooling body having a large cooling capacity.

In Table 1 is given the analytical results obtained for the slag samples by performing fluorescent X-ray analysis on the contact plane thereof with the hollow polygonal column made of metal plates using hot rolled normal steel, while changing the thickness of said metal plates. The slag samples were obtained by immersing the hollow column into a slag at a temperature range of from 1,550 to 1,650° C. for a duration of 1 second. As comparative values, also given in Table 1 are the results obtained by performing the conventional glass bead fluorescent X-ray analysis. As shown herein, it is impossible to obtain a sample having a flat plane in case a metal plate 2 mm in thickness is used because of large deformation occurred on the flat plane. However, in case a metal plate 3 mm or more in thickness is used, results well comparable to those obtained by the conventional methods can be obtained. Further, it can be understood that the use of metal plates 5 mm or more in thickness does not contribute to the improvement in analytical precision, but reversely increases the weight as to impair the handling advantages. Accordingly, it is preferred to use metal plates 5 mm or less in thickness.

TABLE 1

| Thickness of metal plate | Analytical results of the components (%) | | | |
|---|---|---|---|---|
| (mm) | CaO | $Al_2O_3$ | $SiO_2$ | MgO |
| 2* | — | — | — | — |
| 3 | 45.6 | 6.2 | 29.4 | 13.2 |
| 5 | 45.3 | 6.7 | 29.7 | 13.3 |
| 10 | 45.6 | 6.3 | 29.9 | 13.7 |
| Conventional method | 45.3 | 6.5 | 29.5 | 13.5 |

*Metal plate fused to make sampling impossible.

In the method according to the present invention, the time of contact the slag with the polygonal column is extremely shortened, and hence, the column is immediately pulled out after it is immersed into the slag. More specifically, the time duration for immersion is 1 second or less. Which is considerably shorter as compared with several seconds, i.e., the time required in the conventional technique. Accordingly, even if a hollow polygonal column made of a relatively thin metal plates is used, a sample having a smooth surface can be obtained without causing deformation which occurs on contacting the hollow polygonal column with the slag. Furthermore, although the hollow polygonal column is made of thin metal plates, there is no practical disadvantages because the quenched portion need not be thick. That is, the sampler according to the present invention exhibits advantageous effects in that it is sufficiently strong as to surely capture the vigorously fluctuating slag on a flat plane, that is lightweight, and that is superior in operability.

The slag sample must be finished as such that it exhibits a smooth surface. If a sample having a smooth surface is not achieved in fluorescent X-ray analysis, the generated fluorescent X-ray would be partially cut as to lower the analytical precision. To obtain analytical results with an analytical precision having a relative error confined to within 10% from this point of view, it is preferred that the surface roughness of the sampler as expressed by Ra is controlled to 20 μm or less. In addition that the sample is flat, it is necessary that the plane thereof is plane. The analytical precision is impaired if the incident angle of incident X-ray differs depending on the position. Thus, the surface of the hollow polygonal column must be finished to a smooth surface necessary for fluorescent X-ray analysis, and the plane of the slag in contact with this smooth surface is used as the analytical plane. In this case, an area of the smooth sample plane covering the analytical width of the fluorescent X-ray analysis suffices the requirement, and, in general, an area 10 $mm^2$ or larger on the sample is sufficient.

In FIG. 1 is shown an example of slag sampler preferably used for preparing the analytical sample satisfying the above required characteristics. In the present example, a steel hollow tetragonal column 1 having flat planes as the surrounding planes for use in quenching the slag is supported by a holder (paper tube) 4. To the surrounding plane of the hollow tetragonal column 1 is applied a slag releasing agent 2 as to provide smooth surfaces. By taking into consideration the advantages in handling at the operation site, and in order to obtain samples having further improved in smoothness, the hollow tetragonal column is provided as such having a thickness of 3 mm and a side each about 50 mm in length. Furthermore, the holder 4 is fixed to the hollow tetragonal column 1 so that the sampler may be supported thereby. The front end of the sampler is filled with mortar 3 so that no molten steel and the like might intrude into the inside of the sampler. In the present application, a hollow polygonal (tetragonal) closed tube having a steel bottom portion may be used in the place of mortar.

The surface of the sampler is coated with a slag releasing agent 2. The slag releasing agent is made from an oxide of a metal such as iron, manganese, etc., or from ceramics. The slag releasing agent improves the wettability in sampling, and easily allows the cooled and solidified slag to be stripped off from the sampler. Accordingly, the sample can be easily imparted with a sufficiently large area and a smooth plane. Furthermore, by selecting the oxide or the ceramics as such that it may be different from the analytical elements contained in the slag, the precision of slag analysis remains without being impaired. However, it should be noted that the surface smoothness of the solidified slag depends on the surface smoothness of the releasing agent; hence, the surface of the releasing agent must be finished as such that the smoothness necessary for fluorescent X-ray analysis should be realized.

In the example above, the hollow tetragonal column may be freely changed into a triangular column or polygonal columns having five sides or more. Furthermore, a hot rolled steel sheet having hot scales can be used as the member constituting the hollow polygonal column, such that the scales generated on the surface may be used as the slag releasing agent. The height of the hollow tetragonal column 1 is preferably 500 mm or more, so that the slag sample can be surely sampled even in case the slag undergoes fluctuation.

EXAMPLES

In FIG. 1 is shown the apparatus according to the present invention, and Table 2 shows the results of the analysis performed by using the apparatus. The result obtained by compositional analysis using fluorescent X-ray analysis on a glass bead prepared by a conventional method as well as the result using the sampler according to an embodiment of the present invention but analyzing the non-contact sample plane are also given in Table 2. From the results shown in Table 2, it can be understood that the analytical result obtained by the present invention is in good agreement with the result obtained by the glass bead method. Furthermore, it is also understood that, even if the sampler according to the present invention should be used, the analytical results obtained on a contact plane give erroneous values due to the segregation; i.e., the value is lower for CaO, $Al_2O_3$, and $SiO_2$, but is higher for MgO. By using the method according to the present invention, the time necessary for the compositional analysis of slag, which formerly took at least 20 minutes, was shortened within 3 minutes.

TABLE 2

| Method of analysis | Analytical results of the components (%) | | | |
|---|---|---|---|---|
| | CaO | $Al_2O_3$ | $SiO_2$ | MgO |
| Present invention | 45.4 | 6.7 | 29.2 | 12.6 |
| Conventional method | 45.7 | 6.5 | 29.1 | 12.6 |
| Non-contact plane | 39.0 | 4.0 | 25.8 | 28.3 |

APPLICABILITY IN INDUSTRY

According to the constitution of the present invention as described in detail above, samples free from segregation can be prepared extremely rapidly from the fluctuating molten slag in the refining furnace with improved operability and yet, surely. Thus, the refining process can be controlled based on the slag composition during the smelting process of a steel and the like.

While the invention has been described in detail by making reference to specific examples, it should be understood that various changes and modifications can be made without departing from the scope and the spirit of the present invention.

What is claimed is:

1. A method of preparing a slag sample for use in fluorescent X-ray analysis, which comprises immersing a metallic hollow polygonal column having a smooth outer surface into a molten slag and immediately pulling it up, and then using the contact plane of the slag adhered on the outer surface of the hollow polygonal column as the analytical plane.

2. A method of preparing a slag sample for use in fluorescent X-ray analysis as claimed in claim 1, wherein the hollow polygonal column is a hollow tetragonal column.

3. A method of preparing a slag sample for use in fluorescent X-ray analysis as claimed in claim 1, wherein the hollow polygonal column is immersed for 1 second or less.

4. A slag sampler for use in fluorescent X-ray analysis, which is a hollow polygonal column comprising a smooth outer surface, and the member constituting the hollow polygonal column is a metal having a thickness of 3 mm or greater.

5. A slag sampler for use in fluorescent X-ray analysis as claimed in claim 4, wherein the outer surface of said hollow polygonal column is coated with a releasing agent.

6. A slag sampler for use in fluorescent X-ray analysis as claimed in claim 5, wherein said hollow polygonal column is a hollow tetragonal column.

7. A slag sampler for use in fluorescent X-ray analysis as claimed in claim 4, wherein said hollow polygonal column is a hollow tetragonal column.

8. A slag sampler for use in fluorescent X-ray analysis as claimed in claim 4, wherein the metal has a thickness of 5 mm or less.

9. A slag sampler for use in fluorescent X-ray analysis as claimed in claim 8, wherein the hollow polygonal column has a height of 500 mm or more.

10. A slag sampler for use in fluorescent X-ray analysis as claimed in claim 4, wherein the hollow polygonal column has a height of 500 mm or more.

11. A method of analyzing a slag sample by fluorescent X-ray analysis comprising the steps of:

immersing a metallic hollow polygonal column having a smooth outer surface into a molten slag;

immediately withdrawing the hollow polygonal column having solidified slag adhered to the outer surface of the hollow polygonal column from the molten slag;

removing the solidified slag from the outer surface of the hollow polygonal column; and subjecting the plane of the solidified slag which was in contact with the outer surface of the hollow polygonal surface to fluorescent X-ray analysis.

12. The method as claimed in claim 11, wherein the hollow polygonal column comprises a hollow tetragonal column.

13. The method as claimed in claim 11, wherein the hollow polygonal column comprises metal walls having a thickness of 3 mm or more.

14. The method as claimed in claim 13, wherein the metal walls have a thickness of 5 mm or less.

15. The method as claimed in claim 14, wherein the hollow polygonal column has a height of 500 mm or more.

16. The method as claimed in claim 13, wherein the hollow polygonal column has a height of 500 mm or more.

17. The method as claimed in claim 11, wherein the outer surface of the hollow polygonal column is coated with a slag release agent.

18. The method as claimed in claim 11, wherein the hollow polygonal column is immersed for 1 second or less.

* * * * *